United States Patent
Harutyunyan

(10) Patent No.: US 9,616,376 B2
(45) Date of Patent: Apr. 11, 2017

(54) CLASS OF TUNABLE GAS STORAGE AND SENSOR MATERIALS

(71) Applicant: Honda Motor Co., Ltd., Tokyo (JP)

(72) Inventor: Avetik R. Harutyunyan, Columbus, OH (US)

(73) Assignee: HONDA MOTOR CO., LTD., Tokyo (JP)

( * ) Notice: Subject to any disclaimer, the term of this patent is extended or adjusted under 35 U.S.C. 154(b) by 0 days.

(21) Appl. No.: 14/203,395

(22) Filed: Mar. 10, 2014

(65) Prior Publication Data

US 2014/0194658 A1    Jul. 10, 2014

Related U.S. Application Data

(62) Division of application No. 12/463,555, filed on May 11, 2009, now abandoned.

(51) Int. Cl.
*B01D 53/04* (2006.01)
*C01B 3/00* (2006.01)
(Continued)

(52) U.S. Cl.
CPC ............ *B01D 53/04* (2013.01); *B01D 53/32* (2013.01); *B01J 20/20* (2013.01); *B01J 20/205* (2013.01);
(Continued)

(58) Field of Classification Search
CPC ..... C01B 3/0021; C01B 21/24; C01B 3/0026; C01B 3/0031; C01B 3/0078; B01D 53/04; B01D 53/32; B01D 53/02; B01D 2253/102; B01D 2257/504; B01D 2257/404; B01D 2257/104; B01D 2257/108; B01D 2257/502; B01D 2253/304; B01D 2253/25; B01D 2257/102; B01D 2257/7025; B01D 2253/34; B01J 37/0236; B01J 20/3295; B01J 20/324; B01J 20/3441; B01J 23/745; B01J 20/20;
(Continued)

(56) References Cited

U.S. PATENT DOCUMENTS 2,985,519 A    5/1961    Kelemen
5,653,951 A    8/1997    Rodriguez et al.
(Continued)

FOREIGN PATENT DOCUMENTS

JP    2003-225561 A    8/2003
JP    2004-059409 A    2/2004
(Continued)

OTHER PUBLICATIONS

Chen et al, "High H2 Uptake by Alkali-Doped Carbon Nanotubes Under Ambient Pressure and Moderate Temperature," Science 285, 91 1991 pp. 91-93.*
(Continued)

*Primary Examiner* — Anthony J Zimmer
(74) *Attorney, Agent, or Firm* — Arent Fox LLP

(57) ABSTRACT

The electronic structure of nanowires, nanotubes and thin films deposited on a substrate is varied by doping with electrons or holes. The electronic structure can then be tuned by varying the support material or by applying a gate voltage. The electronic structure can be controlled to absorb a gas, store a gas, or release a gas, such as hydrogen, oxygen, ammonia, carbon dioxide, and the like.

20 Claims, 1 Drawing Sheet

(51) Int. Cl.

| | | |
|---|---|---|
| *B01D 53/32* | (2006.01) | |
| *B01J 20/20* | (2006.01) | |
| *B01J 20/32* | (2006.01) | |
| *B01J 20/34* | (2006.01) | |
| *B01J 23/745* | (2006.01) | |
| *B01J 37/02* | (2006.01) | |
| *B82Y 30/00* | (2011.01) | |
| *C01B 21/24* | (2006.01) | |
| *B01D 53/02* | (2006.01) | |
| *B82Y 40/00* | (2011.01) | |

(52) U.S. Cl.
CPC ......... *B01J 20/324* (2013.01); *B01J 20/3295* (2013.01); *B01J 20/3441* (2013.01); *B01J 23/745* (2013.01); *B01J 37/0236* (2013.01); *B82Y 30/00* (2013.01); *C01B 3/0021* (2013.01); *C01B 3/0026* (2013.01); *C01B 3/0031* (2013.01); *C01B 3/0078* (2013.01); *C01B 21/24* (2013.01); *B01D 53/02* (2013.01); *B01D 2253/102* (2013.01); *B01D 2253/25* (2013.01); *B01D 2253/304* (2013.01); *B01D 2253/34* (2013.01); *B01D 2257/102* (2013.01); *B01D 2257/104* (2013.01); *B01D 2257/108* (2013.01); *B01D 2257/404* (2013.01); *B01D 2257/502* (2013.01); *B01D 2257/504* (2013.01); *B01D 2257/7025* (2013.01); *B82Y 40/00* (2013.01); *Y02C 10/08* (2013.01); *Y02C 20/20* (2013.01); *Y02E 60/325* (2013.01); *Y02E 60/327* (2013.01); *Y02P 20/152* (2015.11); *Y02P 20/156* (2015.11)

(58) Field of Classification Search
CPC ........ B01J 20/205; B82Y 30/00; B82Y 40/00; Y02P 20/156; Y02P 20/152; Y02C 20/20; Y02C 10/08; Y02E 60/325; Y02E 60/327
See application file for complete search history.

(56) References Cited

U.S. PATENT DOCUMENTS

| | | | |
|---|---|---|---|
| 5,973,444 A | 10/1999 | Xu et al. | |
| 6,280,697 B1 | 8/2001 | Zhou et al. | |
| 7,288,576 B2 | 10/2007 | Wang et al. | |
| 2003/0205457 A1 | 11/2003 | Choi et al. | |
| 2004/0099093 A1 | 5/2004 | Harutyunyan et al. | |
| 2004/0104129 A1* | 6/2004 | Gu et al. | 205/775 |
| 2006/0249402 A1 | 11/2006 | Snow et al. | |
| 2007/0092437 A1 | 4/2007 | Kwon et al. | |
| 2007/0145356 A1* | 6/2007 | Amlani et al. | 257/40 |
| 2007/0284631 A1 | 12/2007 | Hsu et al. | |
| 2010/0282245 A1* | 11/2010 | Star et al. | 128/200.14 |
| 2010/0300893 A1 | 12/2010 | Suh et al. | |

FOREIGN PATENT DOCUMENTS

| | | |
|---|---|---|
| JP | 2004-526659 A | 9/2004 |
| JP | 2006-329802 A | 12/2006 |
| JP | 3917871 B2 | 5/2007 |
| JP | 2007-186353 A | 7/2007 |
| JP | 4005511 B2 | 11/2007 |
| JP | 4825968 B2 | 11/2011 |
| WO | WO 0117900 A1 | 3/2001 |
| WO | WO 2005084378 A2 | 9/2005 |
| WO | WO 2008088780 A1 * | 7/2008 |

OTHER PUBLICATIONS

Carey et al., "Advanced Organic Chemistry 3rd Ed." vol. A. Plenum Press, New York, 1990.*
Carey et al., "Advanced Organic Chemistry 3rd Ed." vol. B. Plenum Press, New York, 1990.*
Chambers, A., et al., "Hydrogen Storage in Graphite Nanofibers," J. Phys. Chem. B., vol. 102, pp. 4253-4256, May 1998.
Dillon, A. et al., "Storage of Hydrogen in Single-Walled Carbon Nanotubes," Nature, vol. 386, pp. 377-379, 1997.
Fang, B. et al., "Controllable Synthesis of Hierarchical Nanostructured Hollow Core/Mesopore Shell Carbon for Electrochemical Hydrogen Storage," Langmuir, pp. 12068-12072, vol. 24, 2008.
Fang, B., et al., "Ordered Porous Carbon with Tailored Pore Size for Electrochemical Hydrogen Storage Application," J. Phys. Chem. B., vol. 110, pp. 4875-4880, 2006.
Harutyunyan, A. R. et al., "CVD Synthesis of Single Wall Carbon Nanotubes Under 'Soft' Conditions", American Chemical Society, Nano Letters, vol. 2, No. 5, pp. 525-530, 2002.
International Search Report and Written Opinion of International Application No. PCT/US2010/034059 dated Nov. 19, 2010.
Journet, C. et al., "Large-Scale Production Of Single-Walled Carbon Nanotubes By The Electric-Arc Technique", Nature, vol. 388, pp. 756-758, Aug. 21, 1997.
Kavan, L. et al., "Electrochemical Tuning of Electronic Structure of Single-Walled Carbon Nanotubes: I-situ Raman and Vis-NIR Study," J. Phys. Chem. B., vol. 105, pp. 10764-10771, 2001.
Ndungu, P. et al., "Carbon Nanomaterials Synthesized Using Liquid Petroleum Gas: Analysis Toward Applications in Hydrogen Storage and Production," International Journal of Hydrogen Energy, vol. 33, pp. 3102-3106, 2008.
Nikitin et al., "Hydrogenation of Single-Walled Carbon Nanotubes", Physical Review Letters, vol. 95, 22507-1-4, Nov. 25, 2005.
Ong, K. et al., "A Wireless, Passive Carbon Nanotube-Based Gas Sensor", IEEE Sensors Journal, vol. 2, No. 2, pp. 82-88, Apr. 2002.
Pillai, P. et al., "Electrochemical Storage of Hydrogen in Nanotubular TiO. Arrays," Journal of Power Sources, vol. 161, pp. 524-530, 2006.
Cotton et al., "Advanced Inorganic Chemistry 6th Ed." Wiley, New York, 1999.
Carey et al., "Advanced Organic Chemistry 3rd Ed." vols. A and B, Plenum Press, New York, 1990.

* cited by examiner

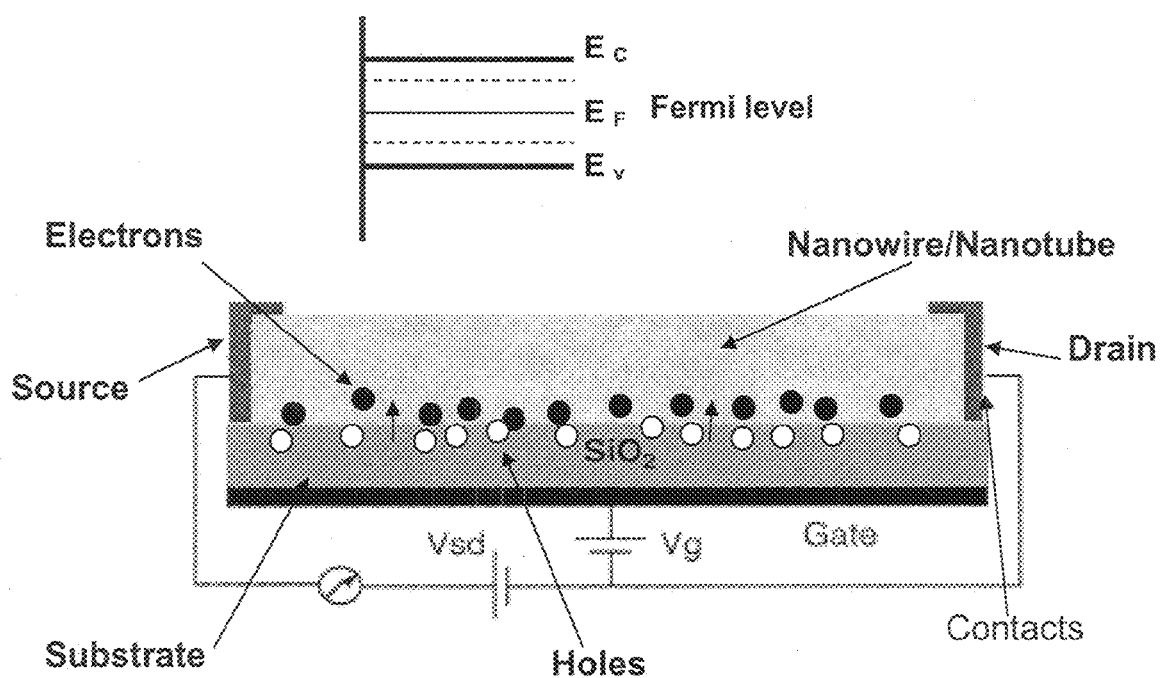

CLASS OF TUNABLE GAS STORAGE AND SENSOR MATERIALS

RELATED APPLICATIONS

This application is a division of application Ser. No. 12/463,555 filed May 11, 2009 which is hereby incorporated by reference in its entirety.

FIELD OF INVENTION

The present invention relates to compositions and methods for reversibly storing gases, in particular by changing the electronic structure of a material thereby tuning the material for storing or sensing a particular gas.

BACKGROUND

A common technique for storing gases is via a liquefaction process where the gas is compressed and cooled from a gas phase into a liquid phase. For example, hydrogen gas liquefies at 20 K at atmospheric pressure, and approximately 70 g/L of the hydrogen gas can be stored in the liquid phase. However, the liquefaction process is very energy intensive and the liquid gas needs to be maintained at the lower temperature requiring specially designed insulated containers and very careful handling.

Another common technique for storing gases is to compress the gas into a suitable vessel. For example, a gas tank pressurized to 35 MPa can store 15 g/L of hydrogen. However, a pressurized-gas tank is heavy, cumbersome, and difficult to transport.

Gases can also be stored by chemically bonding the gas to an appropriate host material. Several types of materials have been studied as hosts, including metals, metal hydrides, glass microspheres and carbon nanotubes. However, the materials investigated so far all have low gas storage capacity. Further, high temperatures are required for releasing the gas, such as from a metal hydride, make these methods unsuitable for commercial use.

Recently, LC resonant sensors have been combined with carbon nanotube materials for utilization as gas sensors. For example, Ong, et al. IEEE Sensors Journal, 2: 82 (2002) described a gas sensor formed of a responsive multi-wall carbon nanotube/silicon dioxide composite layer deposited on a planar LC resonant circuit. The permittivity and/or conductivity of the MWNT/$SiO_2$ composite changes with adsorption of $CO_2$, $O_2$, or $NH_3$ which changes the resonant frequency of the sensor, which can be remotely monitored through a loop antenna. The sensors showed reversible response to $O_2$ and $CO_2$, and an irreversible response to $NH_3$.

Hydrogen can also be stored in carbon nanostructures, such as graphite and carbon nanofibers (A. Dillon et al. Nature 386: 377 (1997), A. Chambers et al. J. Phys. Chem. B 102: 3378 (1998), and U.S. Pat. No. 5,653,951 "Storage of hydrogen in layered nanostructures" to N. Rodriguez and R. Baker). Nanostructures can be defined as atomic structures that have a spatial extent of less than a few hundred nanometers in one, two, or all three dimensions. A class of nanostructures is formed by planar networks, sometimes referred to as layered compounds. The stored hydrogen, however, is not easily released from the carbon nanostructures.

J.P. Patent Publication No. 2003225561A2, published Dec. 8, 2003 "Gas Adsorption Element" by Mitsubishi Heavy Ind. Ltd. discloses that surface of a metal foil can be coated with a carbon material. The carbon material has the capacity for hydrogen occlusion and has high thermal conductivity. The carbon material can be carbon nanotube, carbon nanofiber, or other carbon materials.

The known methods of storing gases are not convenient, require specialized equipment or handling, or high pressures or temperatures to release the trapped gasses. Accordingly, the present invention provides compositions, methods, and processes for the storing or sensing of particular gas where the gas can be easily released.

SUMMARY

The present invention provides compositions, methods, and processes for gas storage and gas sensing. Advantageously, the present invention also provides methods wherein the storage of gas can be reversibly performed under ambient or higher pressure and ambient or higher temperature.

In one aspect, the invention provides methods for modifying materials which can to be used as sorbents in gas storage systems, wherein the material can be modified by changing the potential energy of the surface of the material. The material can be any material capable of storing gas, such as, for example, one-dimensional materials such as carbon nanotubes, carbon nanowires, carbon nanofibers, and the like, or two-dimensional materials such as films. Thus, the material can be selected from carbon, activated carbon, carbon powder, amorphous or disordered carbon, carbon fibers, carbon nanofibers and graphite, films, and the like, as well as metal nanowires and thin films, such as Al, Ni, Ga, As, and their alloys. The invention comprises the doping of the material with electrons or holes thereby changing the structural and electronic properties of the material. The term "doping" refers to an application of a voltage, optionally with the addition of one or more metals to the materials, with the result that the structural and electronic properties of the material are changed. In another aspect, the structural and electronic properties of the material is changed by doping with electrons or holes created by applying gradient of the potentials between the materials and its support.

In another aspect of the invention, the electronic structure of the materials can be modified by doping or by varying the support material such that it has the optimal chemical potential for storing a particular gas or sensing the selected gas. The gas molecules can be released by turning off the gate voltage at ambient temperatures and pressures.

These and other aspects of the present invention will become evident upon reference to the following detailed description. In addition, various references are set forth herein which describe in more detail certain procedures or compositions, and are therefore incorporated by reference in their entirety.

BRIEF DESCRIPTION OF DRAWINGS

FIG. 1 illustrates an apparatus for carrying out the present invention.

DETAILED DESCRIPTION

I. Definitions

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg (1990) "Advanced Organic Chemistry $3^{rd}$ Ed." Vols. A and B, Plenum Press, New York, and Cotton et al. (1999) "Advanced Inorganic Chemistry $6^{th}$ Ed." Wiley, New York.

II. Overview

The present invention discloses compositions, methods, and processes for storing gases and sensing gases. One- or two dimensional materials, such as single-walled carbon nanotubes (SWNTs), multi-walled carbon nanotubes, carbon nanofibers, films, and the like, as well as metal nanowires and thin films, such as Al, Ni, Ga, As, and their alloys are deposited on a support, and doped with electrons by applying a gradient of potentials between the support and the material. The electronic structure of the material can be tuned to be optimal for a particular gas by varying the applied gate voltage and varying the support material. The gas molecules can be released at ambient temperature and ambient pressure by changing the gate voltage.

III. Selection and Synthesis Of Material

The material for use in the present invention can be one-dimensional or two-dimensional. Thus, the material can be carbon nanotubes, activated carbon, carbon powder, amorphous or disordered carbon, carbon fibers, carbon nanofibers, graphite and thin-films. In addition, metal nanowires and thin films, such as Al, Ni, Ga, As, and their alloys can be used in the practice of this invention. The material chosen can be bought from a commercial source or synthesized using known methods. It should be understood that the specific method of forming the material is not critical to the invention, and the described methods are merely exemplary, and not meant to be limiting in any way to the invention.

Graphite is commercially available and has a layered structure, high crystallinity and low surface area. The typical graphite interplanar distance is 0.335 nm.

Carbon fibers are commercially available and made of carbon with a graphite-like structure. Carbon fibers can be commercially made by catalytic decomposition of hydrocarbons. The diameter of carbon fibers is on the order of microns up to centimeters.

Active carbon is commercially available. The activity of activated carbon is related to its large surface area, porosity and low crystallinity. Amorphous carbon is commercially available carbon with low crystallinity.

The single-walled carbon nanotubes (SWNTs) are commercially available, or can be fabricated according to a number of different techniques familiar to those in the art. For example, the SWNTs can be fabricated by the laser ablation method of U.S. Pat. No. 6,280,697, the arc discharge method of Journet et al. Nature 388: 756 (1997), the chemical vapor deposition method where supported metal nanoparticles can be contacted with the carbon source at the reaction temperatures according to the literature methods described in Harutyunyan et al., NanoLetters 2, 525 (2002), and the like. Preferably, the SWNTs are produced by the chemical vapor deposition method.

The chemical vapor deposition (CVD) method for the synthesis of carbon nanotubes uses carbon precursors, such as carbon containing gases. In general, any carbon containing gas that does not pyrolize at temperatures up to 800° C. to 1000° C. can be used. Examples of suitable carbon-containing gases include carbon monoxide, aliphatic hydrocarbons, both saturated and unsaturated, such as methane, ethane, propane, butane, pentane, hexane, ethylene, acetylene and propylene; oxygenated hydrocarbons such as acetone, and methanol; aromatic hydrocarbons such as benzene, toluene, and naphthalene; and mixtures of the above, for example carbon monoxide and methane. In general, the use of acetylene promotes formation of multi-walled carbon nanotubes, while CO and methane are preferred feed gases for formation of single-walled carbon nanotubes. The carbon-containing gas may optionally be mixed with a diluent gas such as hydrogen, helium, argon, neon, krypton and xenon or a mixture thereof.

The catalyst composition for use in CVD can be any catalyst composition known to those of skill in the art. Conveniently, the particles will be of a magnetic metal or alloy, such as, for example, iron, iron oxide, or a ferrite such as cobalt, nickel, chromium, yttrium, hafnium or manganese. The particles useful according to the invention will preferably have an average overall particle size of up to 50 nm to about 1 µm, although, in general, the particle sizes for individual particles can be from about 400 nm to about 1 µm.

The metal catalyst can be selected from a Group V metal, such as V or Nb, and mixtures thereof, a Group VI metal including Cr, W, or Mo, and mixtures thereof, VII metal, such as, Mn, or Re, Group VIII metal including Co, Ni, Ru, Rh, Pd, Os, Ir, Pt, and mixtures thereof, or the lanthanides, such as Ce, Eu, Er, or Yb and mixtures thereof, or transition metals such as Cu, Ag, Au, Zn, Cd, Sc, Y, or La and mixtures thereof. Specific examples of mixture of catalysts, such as bimetallic catalysts, which may be employed by the present invention include Co—Cr, Co—W, Co—Mo, Ni—Cr, Ni—W, Ni—Mo, Ru—Cr, Ru—W, Ru—Mo, Rh—Cr, Rh—W, Rh—Mo, Pd—Cr, Pd—W, Pd—Mo, Ir—Cr, Pt—Cr, Pt—W, and Pt—Mo. Preferably, the metal catalyst is iron, cobalt, nickel, molybdenum, or a mixture thereof, such as Fe—Mo, Co—Mo and Ni—Fe—Mo.

The metal, bimetal, or combination of metals can be used to prepare metal nanoparticles having defined particle size and diameter distribution. The catalyst nanoparticles can be prepared by thermal decomposition of the corresponding metal salt added to a passivating solvent, and the temperature of the solvent adjusted to provide the metal nanoparticles, as described in the co-pending and co-owned U.S. patent application Ser. No. 10/304,316, or by any other method known in the art. The particle size and diameter of the metal nanoparticles can be controlled by using the appropriate concentration of metal in the passivating solvent and by controlling the length of time the reaction is allowed to proceed at the thermal decomposition temperature. The metal salt can be any salt of the metal, and can be selected such that the salt is soluble in the solvent and/or the melting point of the metal salt is lower than the boiling point of the passivating solvent. Thus, the metal salt contains the metal ion and a counter ion, where the counter ion can be nitrate, nitrite, nitride, perchlorate, sulfate, sulfide, acetate, halide, oxide, such as methoxide or ethoxide, acetylacetonate, and the like. For example, the metal salt can be iron acetate ($FeAc_2$), nickel acetate ($NiAc_2$), palladium acetate ($PdAc_2$), molybdenum acetate ($MoAc_3$), and the like, and combinations thereof. The melting point of the metal salt is preferably about 5° C. to 50° C. lower than the boiling point, more preferably about 5° C. to about 20° C. lower than the boiling point of the passivating solvent. The solvent can be an ether, such as a glycol ether, 2-(2-butoxyethoxy)ethanol, H(OCH$_2$CH$_2$)$_2$O(CH$_2$)$_3$CH$_3$, which will be referred to below using the common name dietheylene glycol mono-n-butyl ether, and the like.

In another aspect of the present invention, the material can be multi-walled carbon nanotubes (MWNTs). MWNTs are commercially available or they can be formed according to a chemical vapor deposition method. Using known methods, highly aligned and high purity MWNTs can be produced by the thermal decomposition of a xylene-ferrocene mixture. The xylene serves as the hydrocarbon source and ferrocene provides the iron catalyst nanoparticles that can seed the nanotubes that are grown. According to one process, ferrocene (approximately 6.5%) can be dissolved in xylene and fed into a quartz tube at a flow rate of about 1 ml/hr. The mixture can vaporize upon reaching the end of the pre-heater (maintained at about 200° C.), and the vapors can then be carried into the furnace in an Ar/H$_2$ flow. The furnace is maintained at a temperature (e.g., about 750° C.) that enables the xylene/ferrocene mixture to decompose and form the MWNTs. The nanotubes are harvested from the walls of the furnace and can have a diameter of about 25 nm.

A nanowire refers to a wire having a diameter typically in the range of about one nanometer (nm) to about 500 nm. Nanowires are solid, and can have amorphous structure, graphite like structure, or herringbone structure. The nanowires are periodic only along their axis, and can therefore assume any energetically favorable order in other planes, resulting in a lack of crystalline order.

Nanowires are typically fabricated from a metal or a semiconductor material, and some of the electronic and optical properties of the metal or semiconductor materials are different than the same properties of the same materials in larger sizes. For example, metallic wires having a diameter of 100 nm or less display quantum conduction phenomena, such as the survival of phase information of conduction electrons and the obviousness of the electron wave interference effect. Semiconductor or metal nanowires have attracted considerable attention because of their potential applications in mesoscopic research, the development of nanodevices, for use as gas sensors and field emitters, and the potential application of large surface area structures. For example, U.S. Pat. No. 5,973,444 to Xu et al. discloses carbon fiber-based field emission devices, where carbon fiber emitters are grown and retained on a catalytic metal film as part of the device. Xu et al. disclose that the fibers forming part of the device may be grown in the presence of a magnetic or electric field, as the fields assist in growing straighter fibers.

One technique for fabricating quantum wires utilizes a micro lithographic process followed by metalorganic chemical vapor deposition (MOCVD). This technique may be used to generate a single quantum wire or a row of gallium arsenide (GaAs) quantum wires embedded within a bulk aluminum arsenide (AlAs) substrate. One problem with this technique, however, is that microlithographic processes and MOCVD have been limited to GaAs and related materials. Moreover, this technique does not result in a degree of size uniformity of the wires suitable for practical applications.

Another method of fabricating nanowire systems involves using a porous substrate as a template and filling naturally occurring arrays of nanochannels or pores in the substrate with a material of interest. However, it is difficult to generate relatively long continuous wires having relatively small diameters because as the pore diameters become small, the pores tend to branch and merge, and because of problems associated with filling long pores having small diameters with a desired material.

The nanowires for use in the present invention can be synthesized by providing a substrate, depositing a metalorganic layer on the substrate, and heating the substrate with the metalorganic layer to form nanowires on the substrate. The substrate can be silicon oxide, aluminum oxide, magnesium oxide, glass, mica, silicon, fiberglass, Teflon, ceramics, plastic, or quartz or mixtures thereof. The metalorganic layer can be metal phthalocyanine, such as iron phthalocyanine or nickel phthalocyanine. The metalorganic can be deposited on the substrate as a thin film, and heated under air to form the metal nanowires.

In particular, the nanowires for use in the invention can be synthesized by providing a substrate, depositing a metalorganic layer on the substrate, wherein the metalorganic layer is iron phthalocyanine, nickel phthalocyanine or mixtures thereof, and heating the substrate with the metalorganic layer to form nanowires on the substrate.

In another aspect of the invention, the two-dimensional material can be used, such as thin films. The thin film for use in the present invention preferably contain carbon as a main component. Thus, the carbon thin film can be fullerene, SWNT, or MWNT having a film thickness of 0.5 nm to about 100 nm, preferably a film thickness of about 5 nm to about 80 nm, or even more preferably, a film thickness of 0 at least about 10 nm. The film can contain elements other than carbon, such as boron, nitrogen, Cs, Rb, K, Pd, Li, Al, Co, Fe, Ni, Cu, CrC, MoC, MoO$_3$, WC$_x$, WO$_3$, TiC, SiC, or the like. Preferably, the other element is present at a concentration of about 50 atom percent or less, and more preferably 30 atom percent or less.

The films for use in the invention can be thin amorphous silicon, micro crystalline silicon and amorphous silicon film. These films can be obtained from commercial sources or amorphous silicon film, thin micro crystalline silicon film, thin silicon nitride film can be manufactured using plasma enhanced chemical vapor deposition (PECVD). Typically, the substrate is mounted on the stage inside the vacuum reaction chamber and SiH$_4$ is supplied to the chamber through the gas inlet nozzles of the gas supplying unit. Silicon source gases other than SiH$_4$ such as Si$_2$H$_6$, SiH$_2$Cl$_2$, etc. can also be used, usually at a flow of 0.5 SCCM and a pressure of 70 mTorr. RF power at 40 W is applied to the spiral antenna placed adjacent to the chamber to form inductively coupled plasma. After the substrate temperature reaches 250° C., thin amorphous silicon film is deposited on the substrate.

In another aspect, the thin film can be metal or metal alloys, such as those of palladium, titanium, and the like. Alloys of PdTi can be prepared which exhibit greater changes in electrical resistivity when exposed to concentration of a gas, such as hydrogen. The palladium-titanium alloy can have relative concentration of each in the range from above 0 to below 100% such as 1-99:99-1%. The exact alloy ratio used will depend on the application. For example, if the gas is hydrogen and if the sensor will be exposed to high concentrations of hydrogen, then the amount of Ti in the alloy will be increased. Preferably, the alloy contains between 50 or 60 and 99 atomic % Pd, or more preferably between 70 and 98 atomic % Pd, or even more preferably, between 90 and 98 atomic % Pd. Thin films of the PdTi alloy can be formed by sputtering. Atomic particles of palladium and titanium can be shot onto a substrate. The sputtering rates can be varied to vary the amount of each material present in the alloy. The Pd can be sputtered at a power between 50 W and 450 W. In the preferred form, the Pd is sputtered at a power between 75 W and 300 W. In the more preferred form, the Pd is sputtered a power between 100 W and 200 W. Additional materials may be present in the alloy. These additives include elements such as Cr, Ru, Ag, Au, Zr, Cu, Ir, Al, Hf, Pt and Ni and can be present up to 20 atomic %. Other additives including may also be used. Alloys containing these additives may have less than or greater than 20 atomic % of Pt or Ni. The sputtered particles adhere to the substrate and form a thin film layer on a surface of the substrate.

In one aspect of the invention, the one- or two-dimensional material can be doped with a metal. The metal for doping the material can be an alkali metal such as, for example, Li, Na, K, Rb or Cs, or mixtures of the alkali metals. For example, two or three different metals can be used, preferably a mixture of Li and one additional alkali metal. An exemplary mixture is of Li and K.

The alkali metal salts can include carbonates, nitrates, hydroxides, halogenides, acetates, hydrides, nitrites, or the like. The molar ratio of alkali metal to the carbon materials in the reaction is preferably from about 1:50 to 1:1, more preferably from 1:10 to 1:1, or even more preferably about 1:20 to 1:5.

The doping of alkali metals to the carbon materials can be achieved by solid state reaction between the carbon materials and alkali metal salts. The solid state reaction method preferably involves thoroughly mixing the carbon materials with the alkali metal salt, then subjecting the mixture to high temperature treatment under inert gases, such as helium, nitrogen, argon, and the like, or reductive gases such as hydrogen.

IV. Support

The one- or two-dimensional material can preferably be placed on a support material. The support can be silica, alumina, MCM-41, MgO, $ZrO_2$, aluminum-stabilized magnesium oxide, zeolites, or other supports known in the art, and combinations thereof. For example, $Al_2O_3$—$SiO_2$ hybrid support could be used. In one aspect of the invention, the synthesis of the one- or two-dimensional material can be carried out in the presence of the support material. The support material can be powdered thereby providing small particle sizes and large surface areas. The powdered support material can preferably have a particle size between about 0.01 µm to about 100 µm, more preferably about 0.1 µm to about 10 µm, even more preferably about 0.5 µm to about 5 µm, and most preferably about 1 µm to about 2 µm. The powdered support material can have a surface area of 50 to about 1000 $m^2/g$, more preferably a surface area of about 200 to about 800 $m^2/g$. The powdered oxide can be freshly prepared or commercially available. For example, a suitable $Al_2O_3$ powder with 1-2 µm particle size and having a surface area of 300-500 $m^2/g$ is commercially available from Alfa Aesar of Ward Hill, Mass., or Degussa, N.J. Powdered oxide can be added to achieve a desired weight ratio between the powdered oxide and the initial amount of metal used to form the metal nanoparticles. Typically, the weight ratio can be between about 10:1 and about 15:1. For example, if 100 mg of iron acetate is used as the starting material, then about 320 to 480 mg of powdered oxide can be introduced into the solution. The weight ratio of metal nanoparticles to powdered oxide can be between about 1:1 and 1:10, such as, for example, 1:1, 2:3, 1:4, 3:4, 1:5, and the like.

V. Storing and Releasing Gases

The supported material synthesized above can be used to store or detect a selected gas. In one aspect, the support is provided with a plurality of through holes (FIG. 1) allowing for the movement gas molecules. The shape of the holes is not restricted to a circle but can be shaped as ovals, polygons or slits.

As shown in FIG. 1, the lower part of the support can be connected to the (−) pole of a power supply. The upper part of the support can be connected to the (+) pole of the same power supply, with the one- or two-dimensional material, such as SWNT, MWNT, nanowire, or films deposited on the support. The ability of the material to sense a gas or store a gas can be tuned by selecting the support or by varying the voltage.

The carbon-containing material can be coated on the surface of the surface of the support material, or the carbon-containing material can be directly deposited on the support material. For instance, in one embodiment, the carbon nanotube-containing material can be directly deposited on the support material during the nanotube formation process such that the carbon nanotubes can be directly grown on the surface of the support material. The depth and purity of the nanotube-containing layer is not critical to the invention. For example, in one embodiment, the adsorptive nanostructure-containing layer can be about 0.1 µm to about 100 µm thick, preferably about 0.5 µm to about 10 µm thick, or about 2 µm thick.

In one aspect of the invention, the support can be Si or $SiO_2$ and the carbon-containing material can be SWNTs. A gate voltage is applied to tune the electronic structure of SWNTs such that the selected gas preferentially adsorbs onto the SWNTs. The selected gas can by oxygen ($O_2$), nitrogen ($N_2$), ammonia ($NH_3$), carbon dioxide ($CO_2$), carbon monoxide (CO), methane ($CH_4$), nitrous oxide (NO) and the like. The gate voltage can be from about −100 V to about +100 V, preferably about −50 V to about +50 V, or more preferably about −20 V to about +20 V, and values in between. Thus, for example, if the selected gas is oxygen, the device can be held at a temperature of about 20° C. to about 25° C. at a pressure of about 0.95 atmospheres to about 1.05 atmospheres for about 2 h to about 48 h while applying a gate voltage of about 20 V to about +20 V volts.

In one aspect of the invention, the support can be Si or $SiO_2$ and the carbon-containing material can be nanowires. A gate voltage is applied to tune the electronic structure of nanowires such that the selected gas preferentially adsorbs onto the nanowires. Thus, for example, if the selected gas is hydrogen, the device can be held at a temperature of about 20° C. to about 25° C. at a pressure of about 0.95 atmospheres to about 1.05 atmospheres for about 2 h to about 48 h while applying a gate voltage of about −10 v to about +15 v volts.

The gas thus stored can be released by changing the voltage. In one aspect, the voltage is decreased or increased by about 1% to about 50% over the optimal voltage in order to controllably release the trapped gas. For example, the adsorbed gas can be released over a time period of hours to days by decreasing the voltage by about 10%, or more rapidly by decreasing the voltage by about 25%, or the gas can be released over a time period of a few seconds to a few hours by completely turning off the voltage.

In another aspect of the invention, the ability of the carbon-containing material to sense a gas or store a gas can be tuned by including metals in the carbon-containing material. For example, the carbon materials can be doped with Li, Na, or K. The carbon materials thus doped can adsorb hydrogen, oxygen, carbon monoxide or carbon dioxide, for example in the temperature range of about 0° C. to about 40° C., preferably at about 20° C. to about 25° C., and at pressures of about 0.5 atmospheres to about 3 atmospheres, preferably at about 0.9 atmospheres to about 1.5 atmospheres, when a voltage is applied.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

Example 1

Preparation of the Supported Catalyst

Catalysts were prepared by impregnating support materials in metal salt solutions. In a typical procedure, $Fe(NO_2)_2$ was used at a molar ratio of Fe:Al of 1:2. Under a nitrogen atmosphere, $Fe(NO_2)_2$ was added to water in the molar ratio of 1 mM:20 mM. Then aluminum nitrite was added to the metal salt containing aqueous solution. The reaction mixture was mixed using a mechanical stirrer under the nitrogen atmosphere, and heated under reflux for 90 minutes. The reaction was cooled to about 60° C. while flowing a stream of $N_2$ over the mixture to remove the solvent. A black film formed on the walls of the reaction flask. The black film was collected and ground with an agate mortar to obtain a fine black powder.

Example 2

Synthesis of Carbon Nanotubes

Carbon nanotubes were synthesized by using the experimental setup described in Harutyunyan et al., NanoLetters 2, 525 (2002). CVD growth of bulk SWNTs used the catalysts prepared in Example 1 and methane as a carbon source (T=800° C., methane gas flow rate 60 sccm). The carbon SWNTs were successfully synthesized with a yield of about 40 wt % (wt % carbon relative to the iron/alumina catalyst). Analysis of transmission electron microscopy (TEM) images of SWNTs produced showed bundles were produced. Raman spectra of carbon SWNTs produced using produced by the method above were obtained using $\lambda=532$ nm and $\lambda=785$ nm laser excitation.

While the invention has been particularly shown and described with reference to a preferred embodiment and various alternate embodiments, it will be understood by persons skilled in the relevant art that various changes in form and details can be made therein without departing from the spirit and scope of the invention. All printed patents and publications referred to in this application are hereby incorporated herein in their entirety by this reference.

We claim:

1. A method for storing a gas comprising:
   providing a device comprising:
   a support deposited on a gate wherein the support is in electrical communication with the gate;
   a carbon-containing material deposited on the support, wherein the support is in electrical communication with the carbon-containing material and wherein the carbon-containing material is separated from the gate by the support; and
   a power supply comprising the gate in electrical communication with the support and the carbon-containing material, wherein the power supply is capable of producing a voltage across the device and wherein the carbon-containing material is configured to adsorb gas responsive to the applied voltage; and
   storing a gas for about 2 to 48 hours by applying a voltage to the device.

2. The method of claim 1 wherein the support comprises $SiO_2$.

3. The method of claim 1 wherein the support comprises Si and $SiO_2$.

4. The method of claim 1 wherein the carbon-containing material is selected from the group consisting of carbon nanotubes and nanowires.

5. The method of claim 4 wherein the carbon-containing material is carbon nanotubes.

6. The method of claim 5 wherein the carbon nanotubes are single-walled carbon nanotubes (SWNTs).

7. The method of claim 6 wherein the SWNTs are semiconducting.

8. The method of claim 1 wherein the carbon-containing material is about 2 μm in length.

9. The method of claim 1 wherein the gas is hydrogen, oxygen, carbon dioxide, carbon monoxide, methane, ammonia or NO.

10. The method of claim 1 wherein the gas is hydrogen.

11. The method of claim 1 wherein the gas is NO.

12. The method of claim 1 further comprising releasing the gas by decreasing the voltage.

13. The method of claim 12 wherein decreasing the voltage comprises decreasing the voltage about 5% to about 50%.

14. The method of claim 1 wherein the power supply is configured to produce a voltage of between −50 V and +50 V across the device.

15. The method of claim 1 wherein the power supply is capable of producing a voltage of between −20 V and +20 V across the device.

16. The method of claim 1 wherein the power supply is capable of producing a voltage of between −15 V and +15 V across the device.

17. The method of claim 1 wherein the power supply is capable of producing a voltage of between −10 V and +10 V across the device.

18. The method of claim 1 wherein the carbon-containing material is doped with a metal.

19. The method of claim 1 wherein the metal is lithium, sodium, or potassium.

20. The method of claim 1 wherein the support comprises a lower part and an upper part and the power supply comprises a negative pole and a positive pole and wherein the negative pole of the power supply comprises the gate and the positive pole of the power supply is connected to the upper part of the support.

* * * * *